United States Patent [19]

Pilgram

[11] 4,299,778
[45] Nov. 10, 1981

[54] N′-CYCLOPROPYL-N-(FLUOROPHENYL)-N-HYDROXYUREAS

[75] Inventor: Kurt H. Pilgram, Modesto, Calif.
[73] Assignee: Shell Oil Company, Houston, Tex.
[21] Appl. No.: 170,419
[22] Filed: Jul. 21, 1980
[51] Int. Cl.³ .................... C07C 83/10; A61K 31/185
[52] U.S. Cl. ............................ 260/500.5 H; 424/315
[58] Field of Search ................................. 260/500.5 H
[56] References Cited

U.S. PATENT DOCUMENTS

| | | | |
|---|---|---|---|
| 3,254,984 | 6/1966 | Johnson | 260/500.5 H |
| 3,277,107 | 10/1966 | Neighbors | 260/500.5 H |
| 3,742,008 | 6/1973 | Krenzer | |
| 3,860,643 | 1/1975 | Richter et al. | 260/545 R |

FOREIGN PATENT DOCUMENTS

| | | | |
|---|---|---|---|
| 1136633 | 12/1968 | United Kingdom | 260/500.5 H |
| 1241047 | 7/1971 | United Kingdom | |

*Primary Examiner*—Joseph E. Evans

[57] ABSTRACT

N′-cyclopropyl-N-(2-fluorophenyl)-2-hydroxyurea and its 2,5-difluorophenyl congener, useful as selective herbicides.

2 Claims, No Drawings

N'CYCLOPROPYL-N-(FLUOROPHENYL)-N-HYDROXYUREAS

DESCRIPTION OF THE INVENTION

It has been found that N'-cyclopropyl-N-(fluorophenyl)-N-hydroxyureas, described by the formula

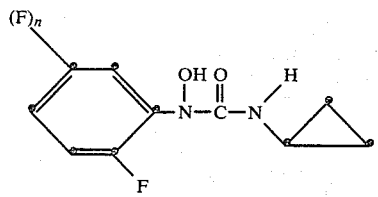

wherein n is zero or one, effectively control weeds in grain sorghum plantings without significant injury to the sorghum plants.

The compounds of the invention have been prepared as described in the following examples. In each case, the identities of the product and any intermediate involved were confirmed by appropriate chemical and spectral analyses.

EXAMPLE 1—N'-cyclopropyl-N-(2-fluorophenyl)-N-hydroxyurea (1)

A mixture of 600 ml of ortho-dichlorobenzene, 103.9 g of sodium azide and 151 g of cyclopropanecarboxylic acid was heated under a nitrogen atmosphere at 110°–130° for 6 hours. The mixture was distilled and the distillate was redistilled to give cyclopropyl isocyanate, (1A), as a liquid, b.p.: 93°–98° C. (1 Torr.).

0.5 g of a commercial rhodium catalyst (5% on charcoal) was added to a stirred mixture of 25 g of 2-fluoronitrobenzene and 250 ml of tetrahydrofuran at room temperature. Then 16.5 g of hydrazine hydrate was added, drop-by-drop, to the stirred mixture, maintained at 15°–20° C. After 20 minutes, another 0.5 g of the rhodium catalyst was added, then another 2 g of hydrazine hydrate was added. The mixture was stirred at 15°–20° C. for 2 hours, then filtered through Celite. The filtrate was extracted with ether, the extract was washed with water, and dried (MgSO$_4$) and the solvent was evaporated. The residue was triturated with ether and hexane, and kept cold until filtered. The filter cake was washed with cold hexane and air-dried to give N-(2-fluorophenyl)hydroxylamine (1B) as a colorless solid, mp: 70°–71° C. It is moderately unstable at room temperature.

8 g of 1A was added, drop-by-drop, to a solution of 9 g of 1B and 1 drop of triethylamine in 50 ml of ether, at 15°–20° C. The resulting mixture was filtered. The solid was washed with cold hexane and dried, to give 1, as a tan solid, m.p.: 135°–138° C.

EXAMPLE 2—N'-cyclopropyl-N-(2,5-difluorophenyl)-N-hydroxyurea (2)

2 was prepared, as a light orange solid, m.p.: 122°–125° C., by procedures similar to those described in Example 1 for the preparation of 1.

Compounds 1 and 2 have been found to be useful for inhibiting growth of unwanted plants, being active with respect to both broadleaved plants and grasses, and being effective when applied either preemergence (applied to the soil before the seeds have sprouted) or postemergence (applied to the foliage of the growing plants).

At the dosages that have effectively controlled unwanted plants, Compounds 1 and 2 have not caused significant injury to grain sorghum plants.

For application to the locus to be treated, the urea preferably is formulated with a carrier, or a surface-active material, or both.

By "carrier" is meant a solid or a fluid material, which may be inorganic or organic and of synthetic or natural origin, with which the urea is mixed or formulated to facilitate its application to the plant, seed, soil or other object to be treated, or its storage, transport or handling.

Suitable solid carriers are natural and synthetic clays and silicates, for example, natural silicas such as diatomaceous earths; magnesium silicates, for example, talcs, magnesium aluminum silicates, for example, attapulgites and vermiculites; aluminum silicates, for example, kaolinites, montmorillonites and micas; calcium carbonates; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols; bitumen, waxes such as, for example, beeswax, paraffin wax, and chlorinated mineral waxes; and solid fertilizers, for example, superphosphates.

Examples of suitable fluid carriers are water, alcohols, such as for example, isopropanol, glycols; ketones such as for example, acetone, methyl ethyl ketone, methyl isobutyl ketone and cyclohexanone; ethers, aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquified normally vaporous gaseous compounds. Mixtures of different liquids are often suitable. The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols and alkylphenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions may be formulated as wettable powders, dusts, granules, solutions, emulsifiable concentrates, emulsions, suspension concentrates and aerosols. Wettable powders are usually compounded to contain 25, 50 and 75% by weight of toxicant and usually contain in addition to solid carrier, 3–10% by weight of a dispersing agent, 15% of a surface-active agent and where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing ½–10% by weight of toxicant. Granules are usually prepared to have a size between 10 and 100 BS mesh (1.676–0.152 mm), and may be manufactured by agglomeration or impregnation techniques. Generally, granules will contain ½–25% by weight toxicant and 0–1% by weight of additives such as stabilizers, slow release modifiers and binding agents. Emulsifiable concentrates usually contain, in addition to the solvent and, when necessary, cosolvent, 10–50% weight per volume toxicant, 2–20% weight per volume emulsifiers and 0–20% weight per volume of appropriate additives such as stabilizers, penetrants and corrosion inhibitors, Suspension concentrates are compounded so as to obtain a stable, non-sedimenting, flowable product and usually contain 10–75% weight toxicant, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate with water, also are suitable. The said emulsions may be of the water-in-oil or of the oil-in-water type, and may have a thick mayonnaise-like consistency.

The compositions may also contain other ingredients, for example other compounds possessing pesticidal, especially insecticidal, acaricidal, herbicidal or fungicidal properties.

Protection of a locus or area from undesirable plants is effected by applying the urea, ordinarily in a composition of one of the aforementioned types, to the foliage of the plants or plant growth medium, e.g., soil in which the plant is growing or in which the seeds are present. The urea, of course, is applied in amounts sufficient to exert the desired action.

The amount of the urea to be used in controlling undesirable vegetation will naturally depend on the condition of the vegetation, the degree of activity desired, the formulation used, the mode of application, the climate, the season of the year, and other variables. Recommendations as to precise amounts are, therefore, not possible. In general, however, application to the locus to be protected of from 0.1 to 10.0 kilograms per hectare of the area will be satisfactory.

EXAMPLES OF HERBICIDAL ACTIVITY

In the following examples, the species of plants that were tested were:
Barnyardgrass (watergrass)—*Echinochloa crus-galli*
Large crabgrass—*Digitaria sanguinalis*
Downy brome—*Bromus tectorum*
Giant foxtail—*Setaria faberii*
Wild oats—*Avena fatua*
Yellow foxtail—*Setaria lutescens*
Hemp sesbania—*Sesbania exaltata*
Jimsonweed—*Datura stramonium*
Ivyleaf morningglory—*Ipomea hederacea*
Wild Mustard—*Brassica kaber*
Redroot pigweed—*Amaranthus retroflexus*
Prickly sida—*Sida spinosa*
Sicklepod—*Cassia obtusifolia*
Velvetleaf—*Abutilon theophrasti*
Garden cress—*Lepidium sativum*
Grain sorghum—*Sorghum vulgare* (Pioneer 265)
Corn—*Zea maize* (deKalb X363)
Cotton—*Gossypium hirsutum* (Acala SJ-2)
Rice—*Oryza sativa* (Calrose)
Soybean—*Glycine max* (Amsoy 71)
Wheat—*Triticum aestivum* (Cajeme 71)
Sugar beet—*Beta vulgaris*
Cocklebur—*Xanthum pennsylvanicum*
Lambsquarters—*Chenopodium album*
Johnsongrass—*Sorghum halepense*

EXAMPLE 1

The preemergence herbicidal activity of Compounds 1 and 2 was evaluated by planting seeds of barnyardgrass, garden cress, downy brome, velvetleaf, yellow foxtail, and sicklepod in test tubes, nominally measuring 25×200 millimeters, filled about three-quarters full of untreated soil, in each case covered on top with about 2.5 cubic centimeters of soil treated with the test compound at the rates of 0.1 and 1 milligram respectively, Table I at Rates I and II, respectively. The dosages were approximately two and twenty pounds of test compound per acre, respectively. The seeds were planted in the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
|---|---|
| 9 | No living tissue |
| 8 | Living tissue, but plant expected to die |
| 7 | Plant badly damaged, but expected to live |
| 6 | Plant badly damaged, but expected to recover completely |
| 5 | Unacceptable damage for crop plants, insufficient damage to weeds |
| 3–4 | Definite damage |
| 1–2 | Plant slightly affected, possibly by the chemical, possibly due to biological variability |
| 0 | No visible effect |

The postemergence activity of Compounds 1 and 2 was evaluated by spraying 10-day old large crabgrass plants, 13-day old redroot pigweed plants, 6-day old downy brome plants, 9-day old velvetleaf plants, 9-day old yellow foxtail plants and 9-day old sicklepod plants to runoff with a liquid formulation of the test compound at the rates of 2.4 milliliters of a 0.025% solution (about one pound of the test compound per acre), designated Rate I in table I, and 2.4 milliliters of a 0.25% solution (about ten pounds of the test compound per acre), designated Rate II in Table I. The sprayed plants were held under controlled conditions of temperature, moisture and light for 7 to 8 days and the effect of the test compound was then evaluated visually, the results being rated on the 0 to 9 scale described above.

The results of the tests are summarized in Table I.

TABLE I

| | Preemergence (Soil) | | | | | | | | | | | | | | Postemergence (Foliar) | | | | | | | | | | | | |
|---|---|---|---|---|---|---|---|---|---|---|---|---|---|---|---|---|---|---|---|---|---|---|---|---|---|---|---|
| | Barnyard-grass | | Garden Cress | | Downy Brome | | Velvetleaf | | Yellow Foxtail | | Sickle-pod | | Crab-grass | | Pigweed | | Johnson-grass | | Velvetleaf | | Yellow Foxtail | | Sickle-pod | |
| | | | | | | | | | | | | Dosage | | | | | | | | | | | | |
| Compound | I | II | I | II | I | II | I | II | I | II | I | II | I | II | I | II | I | II | I | II | I | II | I | II |
| 1 | 8 | 9 | 9 | 9 | 7 | 8 | 9 | 9 | 7 | 8 | 9 | 9 | 2 | 7 | 2 | 9 | 2 | 9 | 3 | 9 | 6 | 9 | 5 | 9 |
| 2 | 7 | 9 | 9 | 9 | 6 | 7 | 9 | 9 | 7 | 8 | 9 | 9 | 6 | 9 | 5 | 9 | 2 | 3 | 5 | 9 | 6 | 9 | 5 | 7 |

EXAMPLE 2

The preemergence herbicidal activity of Compounds 1 and 2 further determined with respect to several common species of weeds, grain sorghum, (and in one case soybeans), by spraying a formulation of the test compound on the soil in which seeds of the test plants had been sown. In each series of tests, the plants were grown in narrow trays and sprayed with the test compound. The solution of the test compound was sprayed over the tray, from one end to the other, the concentration of the test compound in the formulation varying logarithmically from a higher value (5 pounds of the test compound per acre) at one end of the band to a lower value (0.55 pound of the test compound I per acre) at the other end of the band. The effect of the test compound was evaluated visually and reported as the nominal rate of application, in pounds of the test compound per acre of soil band, at which 90% inhibition of the growth of the weeds occurred, this being referred to as the 90% growth inhibition, or $GID_{90}$, dosage. Results of the test, as well as the weed species involved, are set out in Table II.

TABLE II

| | $GID_{90}$ | | | | | | | |
|---|---|---|---|---|---|---|---|---|
| Compound | Barn-yard grass | Downy Brome | Yellow Foxtail | Crab-grass | Velvet-leaf | Johnson-grass | Grain Sorghum | Soybean |
| 1 | — | 0.41 | — | — | 0.15 | — | 2.8 | 0.34 |
| 2 | 1.0 | 0.7 | $-0.55^a$ | $-0.55$ | $-0.55$ | 2.5 | $+5.0^b$ | — |

$^a$"−" means "less than".
$^b$"+" means "more than".

EXAMPLE 3

The postemergence herbicidal activity of Compounds 1 and 2 was further determined with respect to several common species of weeds, and grain sorghum, by spraying a formulation of the test compound on the foliage of young growing plants. In each series of tests, the plants were grown in narrow trays and sprayed with the formulation. The formulation of the test compound was sprayed over the tray, from one end to the other, the concentration of the test compound in the formulation varying logarithmically from a higher value (5 pounds per acre) at one end of the series to a lower value (0.55 pound per acre) at the other end of the series. The effect of the test compound was evaluated visually and reported as the normal rate of application, in pounds of the test compound per acre, at which 90% inhibition of the growth of the weeds occurred, this being referred to as the 90% growth inhibition or $GID_{90}$ dosage. Results of the test, as well as the weed species involved, are in Table III.

TABLE III

| | $GID_{90}$ | | | | | | |
|---|---|---|---|---|---|---|---|
| Compound | Barn-yard grass | Downy Brome | Yellow Foxtail | Crab-grass | Velvet-leaf | Johnson-grass | Grain Sorghum |
| 1 | 2.5 | 5.0 | 1.9 | 1.3 | $-0.55^a$ | $+5.0^b$ | $+5.0$ |
| 2 | $+5.0$ | $+5.0$ | $+5.0$ | 3.7 | $+5.0$ | $+5.0$ | $+5.0$ |

$^a$"−" means "less than".
$^b$"+" means "more than".

EXAMPLE 4

The pre- and postemergence activity of Compound 1 and the preemergence activity of Compound 2 was further determined with respect to a number of crop plants and common species of weeds, using the procedure described in Examples 2 and 3, except that the test compound was applied at three different fixed dosages of the compound per acre, and the results were evaluated with reference to the 0-9 scale described in Example 1. The results of the test are reported in Table IV and V.

TABLE IV

| | Compound 1 | | | | | |
|---|---|---|---|---|---|---|
| | Rating of Effect at Indicated Dosage (lb/acre) | | | | | |
| | Preemergence | | | Postemergence | | |
| Plant Species | 0.25 | 0.50 | 1.0 | 0.5 | 1.0 | 2.0 |
| Corn | 2 | 4 | 6 | 0 | 0 | 0 |
| Cotton | 5 | 6 | 9 | 4 | 6 | 7 |
| Rice | 5 | 5 | 7 | 0 | 2 | 2 |
| Grain Sorghum | 0 | 0 | 2 | 1 | 2 | 2 |

TABLE IV-continued

Compound 1

Rating of Effect at Indicated Dosage (lb/acre)

| Plant Species | Preemergence | | | Postemergence | | |
|---|---|---|---|---|---|---|
| | 0.25 | 0.50 | 1.0 | 0.5 | 1.0 | 2.0 |
| Soybean | 9 | 9 | 9 | 5 | 6 | 7 |
| Sugar beet | 9 | 9 | 9 | 7 | 9 | 9 |
| Wheat | 6 | 8 | 9 | 1 | 1 | 2 |
| Barnyardgrass | 5 | 7 | 9 | 0 | 0 | 0 |
| Crabgrass | 3 | 9 | 9 | 5 | 5 | 6 |
| Downy Brome | 7 | 9 | 9 | 0 | 3 | 5 |
| Giant Foxtail | 5 | 9 | 9 | 0 | 2 | 3 |
| Johnsongrass | 2 | 4 | 6 | 0 | 1 | 3 |
| Wild Oats | 9 | 9 | 9 | 1 | 4 | 6 |
| Yellow Foxtail | 9 | 9 | 9 | 1 | 2 | 3 |
| Cocklebur | 4 | 9 | 9 | 2 | 3 | 5 |
| Hemp sesbania | 9 | 9 | 9 | 4 | 5 | 5 |
| Jimsonweed | 9 | 9 | 9 | 5 | 9 | 9 |
| Morningglory | 9 | 9 | 9 | 2 | 3 | 5 |
| Mustard | 9 | 9 | 9 | 4 | 7 | 9 |
| Pigweed | 9 | 9 | 9 | 1 | 4 | 6 |
| Prickly sida | 9 | 9 | 9 | 4 | 7 | 5 |
| Sicklepod | 9 | 9 | 9 | 4 | 5 | 5 |
| Velvetleaf | 9 | 9 | 9 | 7 | 8 | 9 |

TABLE V

Compound 2

Rating of Effect at Indicated Dosage (lb/acre)

| Plant Species | Preemergence | | |
|---|---|---|---|
| | 0.55 | 1.0 | 2.0 |
| Corn | 0 | 2 | 5 |
| Cotton | 4 | 6 | 8 |
| Rice | 4 | 5 | 7 |
| Grain Sorghum | 1 | 0 | 1 |
| Soybean | 9 | 9 | 9 |
| Sugar beet | 9 | 9 | 9 |
| Wheat | 6 | 7 | 8 |
| Barnyardgrass | 6 | 7 | 9 |
| Crabgrass | 3 | 6 | 9 |
| Downy Brome | 6 | 9 | 9 |
| Giant Foxtail | 3 | 8 | 6 |
| Johnsongrass | 5 | 6 | 9 |
| Wild Oats | 9 | 9 | 9 |
| Yellow Foxtail | 7 | 9 | 9 |
| Cocklebur | 9 | 9 | 9 |
| Hemp sesbania | 9 | 9 | 9 |
| Jimsonweed | 9 | 9 | 9 |
| Morningglory | 6 | 9 | 9 |
| Mustard | 9 | 9 | 9 |
| Pigweed | 9 | 9 | 9 |
| Prickly sida | 9 | 9 | 9 |
| Sicklepod | 9 | 9 | 9 |
| Velvetleaf | 9 | 9 | 9 |

I claim:
1. N'-cyclopropyl-N-(2-fluorophenyl)-N-hydroxyurea.
2. N'-cyclopropyl-N-(2,5-difluorophenyl)-N-hydroxyurea.